United States Patent [19]  [11] 4,169,720
Schacht et al. [45] Oct. 2, 1979

[54] 2-[4-(4-CHLOROPHENOXYMETHYL)-PHENOXY]-PROPIONIC ACID COMPOUNDS AS HERBICIDES

[75] Inventors: Erich Schacht, Seeheim; Gunter Lauterbach, Hahnlein; Werner Mehrhof, Malchen; Jurgen Curtze, Geisenheim-Johannisberg; Gerbert Linden, Ingelheim; Siegmund Lust, Darmstadt; Klaus Thomas, Gau-Algesheim, all of Fed. Rep. of Germany

[73] Assignee: Celamerck GmbH & Co. KG, Ingelheim am Rhein, Fed. Rep. of Germany

[21] Appl. No.: 819,823

[22] Filed: Jul. 28, 1977

[30] Foreign Application Priority Data

Aug. 4, 1976 [DE] Fed. Rep. of Germany ....... 2635099
Aug. 4, 1976 [DE] Fed. Rep. of Germany ....... 2635100
Jun. 30, 1977 [DE] Fed. Rep. of Germany ....... 2729602
Jul. 11, 1977 [DE] Fed. Rep. of Germany ....... 2731214

[51] Int. Cl.$^2$ .................. A01N 9/12; A01N 9/20; A01N 9/24
[52] U.S. Cl. .................. 71/108; 71/98; 71/116; 560/61; 560/63; 560/101; 560/111; 560/164; 560/231; 260/455 R; 260/500.5 H; 260/502.6; 260/559 B; 548/195
[58] Field of Search .............. 560/61, 63; 71/108, 71/116, 98

[56] References Cited

U.S. PATENT DOCUMENTS

| | | | |
|---|---|---|---|
| 2,614,919 | 10/1952 | Warren et al. | 560/61 |
| 2,668,104 | 2/1954 | Eastman | 560/61 |
| 3,968,143 | 7/1976 | Schacht et al. | 560/61 |

Primary Examiner—Joseph E. Evans
Attorney, Agent, or Firm—Hammond & Littell

[57] ABSTRACT

Compounds of the formula

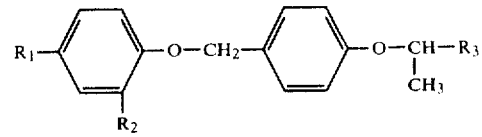

wherein
$R_1$ and $R_2$ are each hydrogen, chlorine or fluorine; and
$R_3$ is —$CH_2OH$, —$CH_2$—O—$COR_4$, —$CH_2$—O—$CONHR_5$, —COOH, —COOCat, —$COOR_6$, —$CONR_7R_8$ or —CO—$SR_9$;
where Cat is one equivalent of an inorganic or organic cation;
$R_4$ is hydrogen or alkyl of 1 to 10 carbon atoms;
$R_5$ is alkyl of 1 to 4 carbon atoms, phenyl or halo-substituted phenyl;
$R_6$ is alkyl of 1 to 10 carbon atoms which may optionally have a chloro, hydroxyl, lower alkoxy, lower alkoxy-lower alkoxy, lower alkylthio, amino, mono-lower alkyl-amino, di-lower alkyl-amino, allyloxy or phenoxy substituent attached thereto; phenyl; benzyl; monochloro-benzyl; dichloro-benzyl; cyclohexyl; 1-ethynyl-cyclohexyl; lower alkenyl; lower alkynyl; —N=C(CH$_3$)$_2$; 2—(2',4',5'-trichloro-phenoxy)-ethyl, 2-(2', 5'-dichloro-4'-bromophenoxy)-ethyl; or

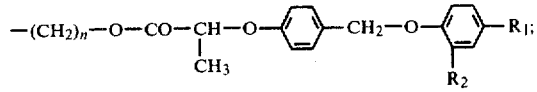

$R_7$ is hydrogen, lower alkyl, hydroxy-lower alkyl, lower alkenyl, lower alkynyl, phenyl, chloro-substituted phenyl, hydroxyl, amino, phenyl-amino or thiazolyl;
$R_8$ is hydrogen, lower alkyl, lower alkenyl or hydroxy-lower alkyl;
$R_9$ is hydrogen or alkyl of 1 to 10 carbon atoms; and
n is an integer from 2 to 6, inclusive.

The compounds are useful as herbicides.

2 Claims, No Drawings

2-[4-(4-CHLOROPHENOXYMETHYL)-PHENOXY]-PROPIONIC ACID COMPOUNDS AS HERBICIDES

This invention relates to certain herbicidal compounds, as well as to novel herbicidal compositions containing said compounds as active ingredients.

More particularly, the present invention relates primarily to herbicidal compositions containing as an active ingredient at least one compound of the formula

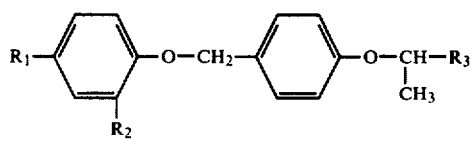
(I)

wherein $R_1$ and $R_2$ are each hydrogen, chlorine or fluorine; and $R_3$ is —CH$_2$OH, —CH$_2$—O—COR$_4$, —CH$_2$—O—CONHR$_5$, —COOH, —COOCat, —COOR$_6$, —CONR$_7$R$_8$ or —CO—SR$_9$;

where Cat is one equivalent of an inorganic or organic cation;

$R_4$ is hydrogen or alkyl of 1 to 10 carbon atoms;

$R_5$ is alkyl of 1 to 4 carbon atoms, phenyl, or halo-substituted phenyl;

$R_6$ is alkyl of 1 to 10 carbon atoms which may optionally have a chloro, hydroxyl, lower alkoxy, lower alkoxy-lower alkoxy, lower alkylthio, amino, mono-lower alkyl-amino, di-lower alkyl-amino, allyloxy or phenoxy substituent attached thereto; phenyl; benzyl; monochloro-benzyl; dichloro-benzyl; cyclohexyl; 1-ethynyl-cyclohexyl; lower alkenyl; lower alkynyl; -N=C(CH$_3$)$_2$; 2-(2', 4', 5'-trichloro-phenoxy)-ethyl, 2-(2', 5'-dichloro-4'-bromo-phenoxy)-ethyl; or

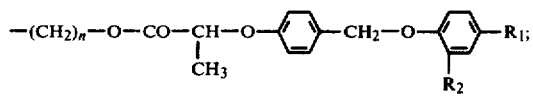

$R_7$ is hydrogen, lower alkyl, hydroxy-lower alkyl, lower alkenyl, lower alkynyl, phenyl, chloro-substituted phenyl, hydroxyl, amino, phenyl-amino or thiazolyl or methoxy;

$R_8$ is hydrogen, lower alkyl, lower alkenyl or hydroxy-lower alkyl;

$R_9$ is hydrogen or alkyl of 1 to 10 carbon atoms; and n is an integer from 2 to 6, inclusive; and to a method of killing weeds therewith.

Formula I above embraces known as well as heretofore unknown compounds.

The known compounds are disclosed in German Offenlegungsschriften 2,342,118 and 2,415,867 and are said to possess useful pharmacological properties, such as anti-hypercholesteremic properties.

The heretofore unknown compounds embraced by formula I are those of the formula

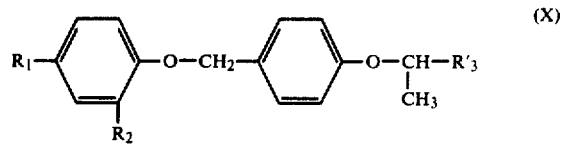
(X)

wherein $R_1$ and $R_2$ are each hydrogen, chlorine or fluorine; and $R_3$ is —CH$_2$—O—COR$_4'$, —CH$_2$—O—CONHR$_5$, —COOR$_6'$, —CONR$_7$R$_8'$ or —CO—SR$_9$;

where $R_4'$ is alkyl of 5 to 10 carbon atoms;

$R_5$ is alkyl of 1 to 4 carbon atoms, phenyl or halo-substituted phenyl;

$R_6'$ is alkyl of 1 to 10 carbon atoms which may optionally have a chloro, hydroxyl, lower alkoxy, lower alkoxy-lower alkoxy, lower alkylthio, amino, mono-lower alkyl-amino, di-lower alkyl-amino, allyloxy or phenoxy substituent attached thereto; phenyl; benzyl; monochloro-benzyl; dichloro-benzyl; cyclohexyl; 1-ethynyl-cyclohexyl; lower alkenyl; lower alkynyl; -N=C(CH$_3$)$_2$; 2-(2', 4', 5'-trichloro-phenoxy)-ethyl, 2-(2', 5'-dichloro-4'-bromo-phenoxy)-ethyl; or

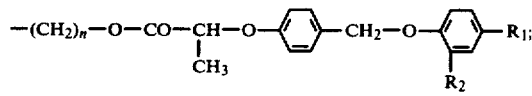

but other than alkyl of 1 to 4 carbon atoms when $R_2$ is hydrogen, $R_7$ is hydrogen, lower alkyl, hydroxy-lower alkyl, lower alkenyl, lower alkynyl, phenyl, chloro-substituted phenyl, hydroxyl, amino, phenyl-amino or thiazolyl;

$R_8$ is hydrogen, lower alkyl, lower alkenyl or hydroxy-lower alkyl, but other than —CH$_2$—CH$_2$OH when $R_2$ is hydrogen;

$R_9$ is hydrogen or alkyl of 1 to 10 carbon atoms; and n is an integer from 2 to 6, inclusive.

A preferred sub-genus of the novel compounds is constituted by those of the formula

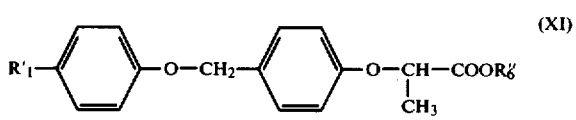
(XI)

wherein $R_1'$ is chlorine or fluorine; and $R_6''$ is alkyl of 5 to 10 carbon atoms; chloro-, hydroxy-, lower alkoxy-, lower alkoxy-lower alkoxy-, lower alkylthio-, amino-, lower alkyl-amino-, di-lower alkyl-amino-, alkyloxy- or phenoxy-substituted alkyl of 1 to 4 carbon atoms; phenyl; benzyl; dichloro-benzyl; cyclohexyl; 1-ethynyl-cyclohexyl; lower alkenyl; lower alkynyl; -N=C(CH$_3$)$_2$; 2-(2', 4', 5'-trichloro-phenoxy)-ethyl, 2-(2',5'-dichloro-4'-bromo-phenoxy)-ethyl; or

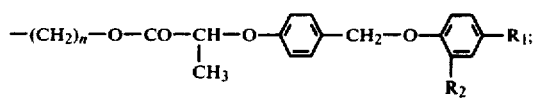

where
- $R_1$ and $R_2$ are each hydrogen, chlorine or fluorine; and
- n is an integer from 2 to 6, inclusive.

Finally, an especially preferred sub-genus of the novel compounds is constituted by those of the formula

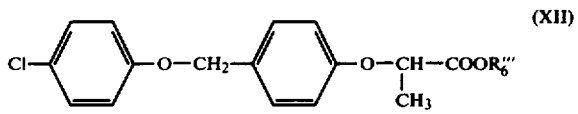

(XII)

wherein $R_6'''$ is lower alkoxy-alkyl or lower alkoxy-lower alkoxy-alkyl, each comprising a total of no more than 8 carbon atoms.

The compounds embraced by formula I may be prepared by the processes described in the aforementioned German Offenlegungsschriften or by other methods involving known chemical synthesis principles. However, the following methods have proved to be most advantageous:

METHOD A

By reacting a compound of the formula

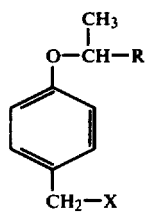

(II)

wherein
- R is carboxyl, alkoxycarbonyl, aryloxycarbonyl, aralkyloxycarbonyl, alkylthiocarbonyl, carbamoyl, hydroxymethyl or acyloxymethyl, and
- X is a substituent which can be split off as an anion, preferably chlorine or bromine, with a phenol of the formula

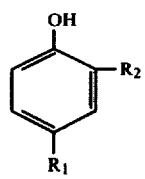

(III)

wherein $R_1$ and $R_2$ have the same meanings as in formula I, in the presence of an acid-binding agent, or with a corresponding phenolate, to form a compound of the formula

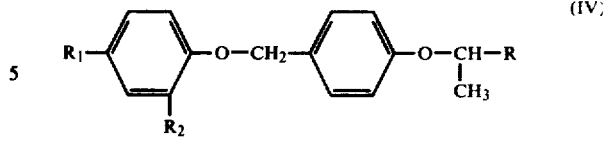

(IV)

wherein $R_1$, $R_2$ and R have the meanings previously defined, and, unless R is already a substituent embraced in the definition of $R_3$ in conjunction with the formula I, subsequently converting R into the desired substituent $R_3$.

The reaction of compound II with compound III is preferably carried out in an inert solvent, such as an alkanol, and at a temperature between 0° C. and the boiling point of the reaction mixture.

Preferred embodiments of R in formula II are those defined for $R_3'$ in conjunction with formula X.

If R in formula IV is an ester or carbamoyl group, hydrolysis, preferably alkaline hydrolysis, yields the corresponding free acid or its salt. Reaction of an ester with an amine of the formula $NHR_7R_8$, where $R_7$ and $R_8$ have the same meanings as in formula I, leads to the corresponding amide or, when $R_7$ is hydroxyl, to the corresponding hydroxamic acid which in turn can be esterified. An initially obtained ester of the formula IV can be converted into another ester by alkali-catalyzed reaction.

Hydrolysis of an ester or amide of the formula IV, preferably with an alkali, leads to a compound of the formula I wherein $R_3$ is —COOH or —COOCat. A salt of such an acid can be converted into an alkyl ester thereof with a conventional alkylating agent, such as a dialkylsulfate.

Reaction of an acid of the formula I with 1,1'-carbonyldiimidazole yields the corresponding imidazolide which in turn may be converted with an alcohol, a mercaptan or an amine into an ester, thioester or amide, respectively. An ester may also be prepared by reacting the corresponding acid with an alcohol in the presence of a carbodiimide. An amide may also be obtained by reacting the acid with an isocyanate.

For the preparation of a compound of the formula I wherein $R_3$ is —$CH_2OH$ or a functional derivative thereof, a corresponding compound of the formula IV wherein R is an esterified carboxyl group is reduced with a complex hydride, preferably with lithium aluminum hydride.

METHOD B

By reacting a phenol of the formula

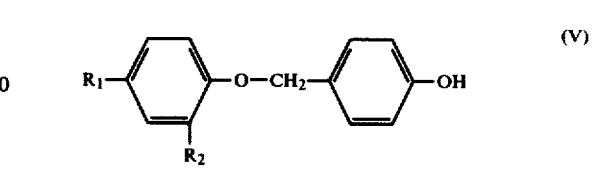

(V)

wherein $R_1$ and $R_2$ have the same meanings as in formula I, in the presence of an acid-binding agent, or a corresponding phenolate, with a propionic acid derivative of the formula

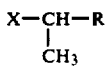   (VI)

wherein R and X have the same meanings as in formula II, to form a compound of the formula IV which may in turn subsequently be converted into various other compounds of the formula I by the diverse methods described under method A.

The reaction is preferably carried out in an inert solvent at a temperature between 0° C. and the boiling point of the reaction mixture.

The starting compounds of the formula II may be obtained from the corresponding alcohol of the formula

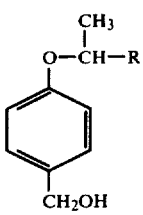   (VII)

wherein R has the same meanings as in formula II, by exchanging the hydroxyl group of the hydroxymethyl substituent for substituent X, as defined in formula II, pursuant to conventional methods.

We have further discovered that compounds of the formula II wherein X is bromine may be obtained by bromination of compounds of the formula

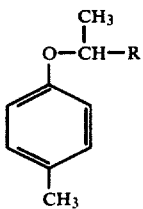   (VIII)

wherein R has the same meanings as in formula II, with bromine/light or bromine/catalyst (azoisobutyric acid nitrile, for example). Contrary to expectation, neither the propionic acid moiety of the molecule nor the benzene is brominated to any appreciable extent. The reaction is carried out in an inert solvent, preferably in a low-polar solvent such as carbon tetrachloride, chloroform, benzene or cyclohexane, and preferably at the boiling point of the reaction mixture.

Compounds of the formula II wherein X is chlorine or bromine may, as we have further discovered, also be obtained by reacting a compound of the formula

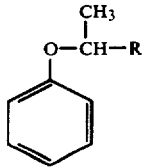   (IX)

wherein R has the same meanings as in formula II, with a halomethylating agent, preferably with formaldehyde/HCl or dichlorodimethyl ether, in an inert solvent such as cyclohexane or benzene, at a temperature of about 0° to 80° C., preferably at room temperature.

A phenol of the formula V may be obtained in known manner by chloromethylating a lower alkyl phenol-carbonate with methyl chloromethyl ether, reacting the resulting product with a phenol of the formula III, and then liberating the phenol of the formula V from the carbonate.

Using the above-described methods, the following compounds of the formula were prepared:

2-[4-(4-Fluorophenoxymethyl)-phenoxy]-propionic acid, m.p. 143°-144° C.;

2-[4-(4-Chlorophenoxymethyl)-phenoxy]-propionic acid, m.p. 156°-158° C.;

2-[4-(2,4-Dichlorophenoxymethyl)-phenoxy]-propionic acid, m.p. 122°-123° C.;

2-[4-(4-Chlorophenoxymethyl)-phenoxy]-propionic acid methyl ester, m.p. 76° C.;

2-[4-(4-Chlorophenoxymethyl)-phenoxy]-propionic acid, ethyl ester, m.p. 47° C.;

2-[4-(4-Chlorophenoxymethyl)-phenoxy]-propionic acid isopropyl ester, m.p. 81° C.;

2-[4-(4-Chlorophenoxymethyl)-phenoxy]-propionic acid n-butyl ester, m.p. 66° C.;

2-[4-(4-Chlorophenoxymethyl)-phenoxy]-propionic acid isobutyl ester, m.p. 75° C.;

2-[4-(4-Chlorophenoxymethyl)-phenoxy]-propionic acid n-amyl ester, m.p. 40° C.;

2-[4-(4-Chlorophenoxymethyl)-phenoxy]-propionic acid n-octyl ester, an oil;

2-[4-(4-Chlorophenoxymethyl)-phenoxy]-propionic acid 2-chloroethyl ester, m.p. 68° C.;

2-[4-(4-Chlorophenoxymethyl)-phenoxy]-propionic acid 3-chloropropyl ester, m.p. 73° C.;

2-[4-(4-Chlorophenoxymethyl)-phenoxy]-propionic acid 2-methoxyethyl ester, m.p. 58° C.;

2-[4-(4-Chlorophenoxymethyl)-phenoxy]-propionic acid 2-(n-butoxy)-ethyl ester, an oil;

2-[4-(4-Chlorophenoxymethyl)-phenoxy]-propionic acid 2-(2-n-butoxyethoxy)-ethyl ester, an oil;

2-[4-(4-Chlorophenoxymethyl)-phenoxy]-propionic acid 2-(2-methoxyethoxy)-ethyl ester, an oil;

2-[4-(4-Chlorophenoxymethyl)-phenoxy]-propionic acid allyl ester, an oil;

2-[4-(4-Chlorophenoxymethyl)-phenoxy]-propionic acid propargyl ester, m.p. 54° C.;

2-[4-(4-Chlorophenoxymethyl)-phenoxy]-propionic acid 2-allyloxyethyl ester, an oil;

2-[4-(4-Chlorophenoxymethyl)-phenoxy]-propionic acid 2-ethylthioethyl ester, an oil;

2-[4-(4-Chlorophenoxymethyl)-phenoxy]-propionic acid 2-hydroxyethyl ester, an oil;

2-[4-(4-Chlorophenoxymethyl)-phenoxy]-propionic acid 1-dimethylamino-2-propyl ester, m.p. 65° C.;

2-[4-(4-Chlorophenoxymethyl)-phenoxy]-propionic acid 2-dimethylaminoethyl ester, m.p. 53° C.;

2-[4-(4-Chlorophenoxymethyl)-phenoxy]-propionic acid cyclohexyl ester, m.p. 72° C.;

2-[4-(4-Chlorophenoxymethyl)-phenoxy]-propionic acid phenyl ester, m.p. 96° C.;

2-[4-(4-Chlorophenoxymethyl)-phenoxy]-propionic acid benzyl ester, m.p. 86° C.;

2-[4-(4-Chlorophenoxymethyl)-phenoxy]-propionic acid 4-chlorobenzyl ester, m.p. 101° C.;

2-[4-(4-Chlorophenoxymethyl)-phenoxy]-propionic acid 2-chlorobenzyl ester, m.p. 68° C.;

2-[4-(4-Chlorophenoxymethyl)-phenoxy]-propionic acid 2,4-dichlorobenzyl ester, m.p. 71° C.;

2-[4-(4-Chlorophenoxymethyl)-phenoxy]-propionic acid 2,6-dichlorobenzyl ester, m.p. 84° C.;
2-[4-(4-Chlorophenoxymethyl)-phenoxy]-propionic acid 2-phenoxyethyl ester, m.p. 77° C.;
2-[4-(4-Chlorophenoxymethyl)-phenoxy]-propionic acid 2-(2,4,5-trichlorophenoxy)-ethyl ester, m.p. 83° C.;
2-[4-(4-Chlorophenoxymethyl)-phenoxy]-propionic acid 2-(4-bromo-2,5-dichlorophenoxy)-ethyl ester, m.p. 99°-100° C.;
2-[4-(4-Chlorophenoxymethyl)-phenoxy]-propionic acid 1-ethynyl-cyclohexyl ester, m.p. 104° C.;
2-[4-(4-Chlorophenoxymethyl)-phenoxy]-propionic acid acetoneoxime ester, an oil;
1,2-Bis-{2-[4-(4-Chlorophenoxymethyl)-phenoxy]-propionyloxy}ethane, an oil;
1,3-Bis-{2-[4-(4-Chlorophenoxymethyl)-phenoxy]-propionyloxy}propane, an oil;
1,6-Bis-{2-[4-(4-Chlorophenoxymethyl)-phenoxy]-propionyloxy}hexane, an oil;
2-[4-(2,4-Dichlorophenoxymethyl)-phenoxy]-propionic acid methyl ester, m.p. 64° C.;
2-[4-(4-Fluorophenoxymethyl)-phenoxy]-propionic acid methyl ester;
2-[4-(4-Fluorophenoxymethyl)-phenoxy]-propionic acid ethyl ester;
2-[4-(4-Chlorophenoxymethyl)-phenoxy]-thiolpropionic acid n-octyl ester, an oil;
2-[4-(4-Chlorophenoxymethyl)-phenoxy]-propionamide, m.p. 143° C.;
2-[4-(4-Chlorophenoxymethyl)-phenoxy]-N-methyl propionamide, m.p. 123° C.;
2-[4-(4-Chlorophenoxymethyl)-phenoxy]-N-n-butyl propionamide, m.p. 98° C.;
2-[4-(4-Chlorophenoxymethyl)-phenoxy]-N-t-butyl propionamide, m.p. 114° C.;
2-[4-(4-Chlorophenoxymethyl)-phenoxy]-N,N-diethyl propionamide, m.p. 52° C.;
2-[4-(4-Chlorophenoxymethyl)-phenoxy]-N-allyl propionamide, m.p. 98° C.;
2-[4-(4-Chlorophenoxymethyl)-phenoxy]-N-1,1-dimethylpropargyl-propionamide, m.p. 127° C.;
2-[4-(4-Chlorophenoxymethyl)-phenoxy]-N-2-hydroxyethyl-propionamide, m.p. 110° C.;
2-[4-(4-Chlorophenoxymethyl)-phenoxy]-N,N-di-(2-hydroxyethyl)propionamide, m.p. 117° C.;
2-[4-(4-Chlorophenoxymethyl)-phenoxy]-N-phenyl propionamide, m.p. 126° C.;
2-[4-(4-Chlorophenoxymethyl)-phenoxy]-N-3-chlorophenyl-propionamide, m.p. 124° C.;
2-[4-(4-Chlorophenoxymethyl)-phenoxy]-N-3,4-dichlorophenyl-propionamide, m.p. 118° C.;
2-[4-(4-Chlorophenoxymethyl)-phenoxy]-N-2-thiazolyl propionamide, m.p. 182° C.;
2-[4-(4-Chlorophenoxymethyl)-phenoxy]-propionic-hydrazide, m.p. 133° C.;
2-[4-(4-Chlorophenoxymethyl)-phenoxy]-propionic-phenylhydrazide, m.p. 144° C.;
2-[4-(4-Chlorophenoxymethyl)-phenoxy]-propionic-hydroxamic acid, m.p. 142° C.;
2-[4-(4-Chlorophenoxymethyl)-phenoxy]-propionic-hydroxamic acid methyl ester, m.p. 113° C.;

The following salts of 2-[4-(4-Chlorophenoxymethyl)-phenoxy]-propionic acid:
Sodium salt, m.p. 250° C.,
Potassium salt, m.p. 222° C.,
Ammonium salt, m.p. 160°-165° C.,
Dimethylammonium salt, m.p. 128°-136° C.,
Diethylammonium salt, m.p. 133° C.
Cyclohexylammonium salt, m.p. 186°-187° C.,
Morpholinium salt, m.p. 123°-124° C.
Imidazolium salt, m.p. 124° C.,
2-Hydroxy-1-propyl-dimethylammonium salt, m.p. 168° C.;
2-[4-(2-Chlorophenoxymethyl)-phenoxy]-propionic acid diethanolamine salt;
2-[4-(2,4-Dichlorophenoxymethyl)-phenoxy]-propionic acid triethanolamine salt;
2-[4-(4-Fluorophenoxymethyl)-phenoxy]-propionic acid dimethylamine salt;
2-[4-(2-Chlorophenoxymethyl)-phenoxy]-propionic acid sodium salt;
2-[4-(2,4-Dichlorophenoxymethyl)-phenoxy]-propionic acid potassium salt;
2-[4-(4-Chlorophenoxymethyl)-phenoxy]-propanol, m.p. 86° C.;
2-[4-(2,4-Dichlorophenoxymethyl)-phenoxy]-propanol;
2-[4-(4-Fluorophenoxymethyl)-phenoxy]-propanol; and
2-[4-(4-Chlorophenoxymethyl)-phenoxy]-propyl acetate.

The following examples further illustrate the present invention and will enable others skilled in the art to understand it more completely. It should be understood, however, that the invention is not limited solely to the particular examples given below.

EXAMPLE 1

Methyl 2-[4-(4-Chlorophenoxy-methyl)-phenoxy]-propionate by method A (a) A mixture consisting of 45 gm (0.37 mol) of 4-hydroxy-benzaldehyde, 111 gm (0.81 mol) of potassium carbonate, 89 ml (0.81 mol) of methyl 2-bromo-propionate and 300 ml of dimethylformanide was heated at 60° C. for 16 hours, while stirring. Thereafter, the reaction mixture was poured into 1 liter of water, and the aquous mixture was extracted with ether. The ethereal extract solution was washed with 1 N potassium hydroxide and then with water, dried and evaporated, leaving 55 gm of methyl 2-(4-formyl-phenoxy)-propionate as an oil, which was purified by passing it through a silicagel column with chloroform as the flow agent.

(b) 44 gm (0.211 mol) of methyl 2-(4-formyl-phenoxy)-propionate were dissolved in 500 ml of methanol, and 8 gm (0.211 mol) of sodium borohydride were added in small portions to the solution. The resulting mixture was stirred at room temperature for 30 minutes and then at 60° C. for 30 minutes. Thereafter, the reaction mixture was evaporated in vacuo to one-half its original volume, poured into water, neutralized with hydrochloric acid, and extracted with ether. The ethereal extract solution was washed, dried and evaporated, leaving 20 gm of methyl 2-(4-hydroxymethyl-phenoxy)-propionate as a colorless oil which was purified on a silicagel column with chloroform as the flow agent.

(c) 12 gm (0.058 mol) of methyl 2-(4-hydroxymethyl-phenoxy)-propionate were dissolved in 60 ml of hexamethylphosphoric acid triamide, the solution was cooled to −10° C., and 4.4 ml (0.06 mol) of thionyl chloride were added dropwise thereto. The resulting mixture was stirred for 30 minutes at 0° C. and then for one hour at 10° C., and subsequently poured into water. The aqueous mixture was extracted with ether, and the extract solution was washed with water, sodium bicarbonate solution and again with water, and dried. The ether was subsequently removed in vacuo at room temperature, leaving methyl 2-(4-chloromethyl-phenoxy)-propionate as a residue.

(d) 5.7 gm (0.044 mol) of 4-chloro-phenol and 10 gm (0.044 mol) of methyl 2-(4-chloromethyl-phenoxy)-propionate were added to a solution of 1.01 gm of sodium in 80 ml of ethanol, and the resulting mixture was refluxed for 6 hours, while stirring. Thereafter, the solvent was removed in vacuo, the residue was admixed with water, and the aqueous mixture was extracted with ether. The ethereal extract solution was washed with 1 N potassium hydroxide and then with water, dried and evaporated, leaving 11 gm of an oily residue which was purified by passing it through a silicagel column with benzene as the flow agent. The initially oily product crystallized upon standing and then had a melting point of 76° C.; it was identified to be the compound of the formula

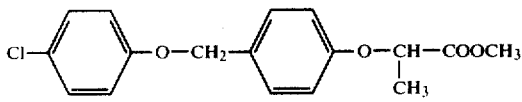

EXAMPLE 2

2-[4-(4-Chlorophenoxy-methyl)-phenoxy]-propionic acid

A mixture consisting of 6 gm of the end product of Example 1 (d), 5 gm of potassium hydroxide and 60 ml of ethanol was refluxed for 2 hours. Thereafter, the solvent was removed in vacuo, the residue was admixed with water and washed with ethyl acetate, and the aqueous alkaline phase was acidified with dilute hydrochloric acid. The precipitate formed thereby was extracted with ethyl acetate, and the organic extract solution was dried and evaporated. 5 gm of a crystalline residue were left behind, which was admixed with hexane and then recovered by suction filtration, yielding 3.8 gm of the free acid which had a melting point of 156°–158° C.

EXAMPLE 3

Methyl 2-[4-(2,4-dichlorophenoxy-methyl)-phenoxy]-propionate by method B 2.3 gm of sodium were dissolved in 100 ml of absolute ethanol, 26.9 gm of 4-(2,4-dichlorophenoxy-methyl)-phenol and 16.7 gm of methyl 2-bromo-propionate were added to the solution, and the mixture was boiled for 3 hours. Thereafter, the reaction solution was evaporated, and the residue was worked up as usual with water and chloroform, yielding 80% of theory of the desired compound named in the heading, which had a melting point of 64° C.

EXAMPLE 4

2-[4-(2,4-Dichlorophenoxy-methyl)-phenoxy]-propionic acid 10 gm of the ester obtained in Example 3 were admixed with 10 gm of potassium hydroxide and 100 ml of ethanol, and the mixture was boiled for 2 hours. Thereafter, the reaction solution was evaporated, the residue was dissolved in water, and the solution was washed with ether and then acidified with hydrochloric acid. The precipitate formed thereby was collected and yielded 90% of theory of the free acid having a melting point of 122°–123° C.

EXAMPLE 5

Ethyl 2-[4-(4-chlorophenoxy-methyl)-phenoxy]-propionate by method A (a) A mixture consisting of 34.8 gm (0.37 mol) of phenol, 111 gm (0.81 mol) of potassium carbonate, 89 ml (0.69 mol) of ethyl 2-bromo-propionate and 200 ml of ethanol was boiled for 12 hours, while stirring. Thereafter, the reaction mixture was filtered, and the filtrate was distilled, yielding 44.2 gm of ethyl 2-phenoxy-propionate, b.p. 93°–94° C. at 0.1 mm Hg.

(b) While vigorously stirring, a strong stream of hydrogen chloride gas was introduced into a suspension of 9.6 gm of paraformaldehyde in 40 ml of concentrated hydrochloric acid until a solution was formed. The temperature was maintained at 15°–20° C. A solution of 38.8 gm (0.2 mol) of ethyl 2-phenoxy-propionate in 20 ml of benzene was then gradually added, and the mixed solution was stirred for 4 hours at 15°–20° C. Thereafter, 30 ml of benzene were added, the organic phase was separated, extracted three times with a semi-saturated aqueous sodium chloride solution, and dried over sodium sulfate, and the benzene was distilled off. The residue was fractionally distilled, yielding 18 gm ethyl 2-(4-chloromethyl-phenoxy)-propionate, b.p. 134°–138° C. at 0.4 mm Hg.

(c) Reaction of the end product of step (b) with 4-chloro-phenol in analogy to Example 1 (d) yielded the ethyl ester named in the heading, which had a melting point of 42° C.

EXAMPLE 6

2-(2,4,5-Trichloro-phenoxy)-ethyl 2-[4-(4-chlorophenoxymethyl)-phenoxy]-propionate A mixture consisting of 2.2 gm of methyl 2-[4-(4-chlorophenoxy-methyl)-phenoxy]-propionate, 2.4 gm of 2-(2,4,5-trichloro-phenoxy)-ethanol and 0.03 gm of sodium was heated at about 120°–150° C. and a pressure of 150 mm Hg for four hours. After cooling, the reaction mixture was briefly boiled with acetone, the cooled solution was filtered, and the solvent was removed from the filtrate in vacuo. The residue was recrystallized from ethanol/water, yielding 1.3 gm (36% of theory) of the compound of the formula

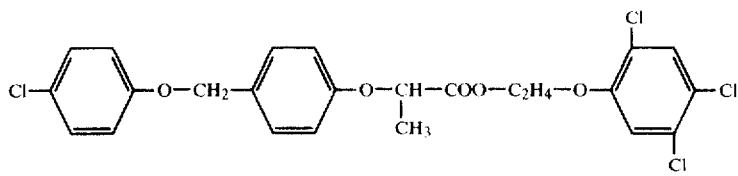

which had a melting point of 83° C.

Using procedures analogous to those described in Examples 1-6, the compounds shown in the following table was also prepared.

Table 1

Cl—⟨⟩—O—CH$_2$—⟨⟩—O—CH(CH$_3$)—R$_3$

| Example No | R$_3$ | m. p. °C. |
|---|---|---|
| 7 | —CO—O—CH$_2$—⟨⟩ | 86 |
| 8 | —CO—O—CH$_2$—CH$_2$—O—⟨Cl,Cl⟩—Br | 99-100 |
| 9 | —CO—O—CH$_2$—CH$_2$—O—CO—CH(CH$_3$)—O—⟨⟩—CH$_2$—O—⟨⟩—Cl | oil |
| 10 | —CO—O—⟨H⟩ | 72 |
| 11 | —CO—O—C$_8$H$_{17}$ | oil |
| 12 | —CO—O—CH$_2$—CH$_2$—O—CH$_2$—CH=CH$_2$ | oil |
| 13 | —CO—O—(CH$_2$)$_3$—O—CO—CH(CH$_3$)—O—⟨⟩—CH$_2$—O—⟨⟩—Cl | oil |
| 14 | —CO—O—(CH$_2$)$_6$—O—CO—CH(CH$_3$)—O—⟨⟩—CH$_2$—O—⟨⟩—Cl | oil |

EXAMPLE 15 n-Butyl 2-[4-(4-chlorophenoxy-methyl)-phenoxy]-propionate

A mixture consisting of 6.4 gm of the end product of Example 1 (d), 50 ml of n-butanol and 0.03 gm of sodium was refluxed for 4 hours, and the reaction mixture was allowed to stand overnight. The precipitate which had formed was separated by suction filtration, and the filtrate was evaporated to dryness in vacuo. The evaporation residue was recrystallized from ethanol/water, yielding 4.5 gm (62% of theory) of the ester named in the heading, which had a melting point of 66° C.

The following esters were prepared in analogous manner from the methyl ester and the corresponding alkanol:

Isobutyl 2-[4-(4-chlorophenoxy-methyl)-phenoxy]-propionate, m.p. 75° C.; and n-Amyl 2-[4-(4-chlorophenoxy-methyl)-phenoxy]-propionate, m.p. 40° C.

EXAMPLE 16

Isopropyl 2-[4-(4-Chlorophenoxy-methyl)-phenoxy]-propionate 6.1 gm of 2-[4-(4-chlorophenoxy-methyl)-phenoxy]-propionic acid was dissolved in 50 ml of absolute tetrahydrofuran, and 3.2 gm of 1,1'-carbonyldiimidazole were added to the solution. The resulting mixture was heated for a short time and was then allowed to stand at room temperature for 4 hours. Thereafter, the reaction mixture was admixed with 2.4 gm of isopropanol, and the mixture was refluxed for one hour, evaporated in vacuo in a rotary evaporator, and the oily residue was recrystallized from ethanol/water, yielding 4.5 gm (65% of theory) of the ester named in the heading, which had a melting point of 81° C.

Using analogous procedures, the esters shown in the following table were also prepared:

Table II

Cl—⟨⟩—O—CH$_2$—⟨⟩—O—CH(CH$_3$)—R$_3$

| Example No | R$_3$ | m. p. °C. |
|---|---|---|
| 17 | —CO—O—CH(CH$_3$)—CH$_2$—N(CH$_3$)$_2$ | 65 |
| 18 | —CO—O—CH$_2$—CH=CH$_2$ | 41 |
| 19 | —CO—O—CH$_2$—CH$_2$—O—CH$_3$ | 58 |
| 20 | —CO—O—CH$_2$—⟨Cl⟩ | 68 |
| 21 | —CO—O—CH$_2$—⟨Cl,Cl,Cl⟩ | 84 |
| 22 | —CO—O—CH$_2$—⟨⟩—Cl | 101 |
| 23 | —CO—O—CH$_2$—⟨Cl,Cl⟩ | 71 |
| 24 | —CO—O—C$_2$H$_5$ | 41 |
| 25 | —CO$_2$—C$_6$H$_5$ | 96 |
| 26 | —CO—O—N=C(CH$_3$)$_2$ | oil |

Table II-continued

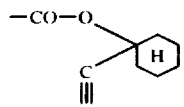

| Example No | R₃ | m. p. °C |
|---|---|---|
| 27 | 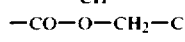 —CO—O | 104 |
| 28 | —CO—O—CH₂—CH₂—Cl | 68 |
| 29 | —CO—O—CH₂—CH₂—CH₂—Cl | 73 |
| 30 | —CO—O—CH₂—CH₂—O—C₆H₅ | 77 |
| 31 | —CO—O—CH₂—C≡CH | 54 |
| 32 | —CO—O—CH₂—CH₂—N(CH₃)₂ | 53 |

EXAMPLE 33

2-[4-(4-Chlorophenoxy-methyl)-phenoxy]-propionic acid amide 6.4 gm of methyl 2-[4-(4-chlorophenoxy-methyl)-phenoxy]-proprionate were dissolved in 100 ml of warm ethanol, 50 ml of a concentrated aqueous ammonia solution were added, and the mixture was slowly heated to its boiling point on a water bath. After a clear solution had formed, 20 ml more of the ammonia solution were added until the solution became turbid, whereupon the mixture was refluxed for 30 minutes. Thereafter, the reaction mixture was allowed to cool, and the crystallizate which had separated out was collected by suction filtration and washed with ethanol/water, yielding 3.5 gm (37% of theory) of the compound of the formula

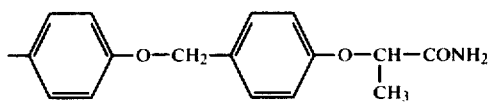

which had a melting point of 143° C.

Using an analogous procedure, the following amides were also prepared:

2-[4-(4-Chlorophenoxymethyl)-phenoxy]-propionic acid hydrazide, m.p. 133° C.;

2-[4-(4-Chlorophenoxymethyl)-phenoxy]-propionic acid 2-hydroxy ethylamide, m.p. 111° C.; and 2-[4-(4-Chlorophenoxymethyl)-phenoxy]-propionic acid diethanolamide, m.p. 117° C.

EXAMPLE 34

2-[4-(4-Chlorophenoxy-methyl)-phenoxy]-propionic acid diethylamide 6.1 gm of 2-[4-(4-chlorophenoxy-methyl)-phenoxy]-propionic acid were dissolved in 50 ml of absolute tetrahydrofuran, 3.24 gm of 1,1'-carbonyldiimidazole were added to the solution, and the mixture was heated for a short time and then allowed to stand for about 4 hours at room temperature. Thereafter, 1.5 gm of diethylamine were added, and the mixture was allowed to stand overnight. Subsequently, the tetrahydrofuran was evaporated in vacuo in a rotary evaporator, and the residue was stirred with warm toluene. The imidazole was then caused to crystallize by scratching. The mixture was allowed to stand for 3 hours, was then suction filtered, and the solvent was removed in vacuo. The oily residue was caused to crystallize by trituration with water, yielding 4.5 gm (62% of theory) of the diethylamide named in the heading, which had a melting point of 52° C.

The cyclohexylamine was prepared in analogous manner with cyclohexylamine, except that after the tetrahydrofuran was distilled off, the residue was recrystallized from ethanol/water. Yield: 5.8 gm (75% of theory); m.p. 138° C.

The amides shown in the following table were prepared in analogous manner.

Table III

| Example No | R₃ | m. p. °C |
|---|---|---|
| 35 | —CO—NH—CH₂—CH=CH₂ | 98 |
| 36 | —CO—N(CH₂—CH=CH₂)₂ | oil |
| 37 | —CO—NH—(CH₂)₃—N(C₄H₉)₂ | 58 |
| 38 | —CO—NH—C(CH₃)₂—C≡CH | 127 |
| 39 | —CO—NH—C(CH₃)₃ | 114 |
| 40 | —CO—NH—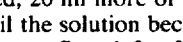 (benzothiazolyl) | 182 |

EXAMPLE 41

2-[4-(4-Chlorophenoxy-methyl)-phenoxy]-propionic acid n-butylamide 6.4 gm of methyl 2-[4-(4-chlorophenoxy-methyl)-phenoxy]-propionate were dissolved in 60 ml of methanol, 6.0 gm of n-butylamine were added to the solution, and the mixture was heated in an autoclave for 4 hours at a pressure of 15–16 atmospheres gauge. After cooling, the solvent was distilled off in vacuo, and the residue was recrystallized from ethanol, yielding 2.8 gm (39% of theory) of the amide named in the heading, which had a melting point of 98° C.

2-[4-(4-Chlorophenoxy-methyl)-phenoxy]-propionic acid phenylhydrazide was prepared in analogous manner from the methyl ester and phenylhydrazine.

EXAMPLE 42

2-[4-(4-Chlorophenoxy-methyl)-phenoxy]-propionic acid anilide

A mixture consisting of 6.1 gm of 2-[4-(4-chlorophenoxy-methyl)-phenoxy]-propionic acid, 2.38 gm of phenylisocyanate and 50 ml of absolute toluene was refluxed for 3 hours. Thereafter, the toluene was distilled off in vacuo, and the residue was recrystallized from ethanol, yielding 3.5 gm (46% of theory) of the anilide named in the heading, which had a melting point of 126° C.

The following amides were prepared in analogous manner:

2-[4-(4-Chlorophenoxymethyl)-phenoxy]-propionic acid methylamide, m.p. 123° C.;

2-[4-(4-Chlorophenoxymethyl)-phenoxy]-propionic acid 3-chloroanilide, m.p. 124° C.; and 2-[4-(4-Chlorophenoxymethyl)-phenoxy]-propionic acid 3,4-dichloroanilide, m.p. 118° C.

EXAMPLE 43

Ethylmercaptoethyl 2-[4-(4-chlorophenoxy-methyl)-phenoxy]-propionate

A mixture consisting of 6.4 gm of methyl 2-[4-(4-chlorophenoxy-methyl)-phenoxy]-propionate and 2.12 gm of 2-ethylmercapto-ethanol was heated to 100° C. on an oil bath, 0.02 gm of sodium was added to the hot mixture, and it was then heated at 150° C. for five hours, the pressure being periodically reduced to 150 mm Hg. Thereafter, the reaction product was isolated as an oil, yielding 6.0 gm (76% of theory) of the ester named in the heading.

EXAMPLE 44

Thiooctyl 2-[4-(4-Chlorophenoxy-methyl)-phenoxy]-propionate

A mixture consisting of 2-[4-(4-chlorophenoxymethyl)-phenoxy]-propionic acid, 50 ml of tetrahydrofuran and 3.24 gm of 1,1'-carbonyldiimidazole was heated for a short time and was then allowed to stand for 4 hours at room temperature. Thereafter, 2.92 of octyl mercaptan were added, and the mixture was refluxed for one hour. Subsequently, the solvent was distilled off, the residue was extracted with warm ethanol/water, and the separated oil was dried in vacuo, yielding 5.5 gm (63% of theory) of the compound of the formula

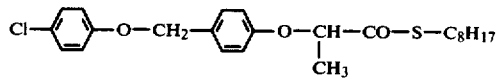

EXAMPLE 45

2-[4-(4-Chlorophenoxy-methyl)-phenoxy]-propionic hydroxamic acid

A solution of 1.4 gm of hydroxylamine hydrochloride in 30 ml of methanol was admixed with 20 ml of a 1 N sodium methylate solution, and the mixture was placed on an ice bath for about 5 minutes. Thereafter, the sodium chloride which had separated out was removed by suction filtration, and the filtrate was added to a solution of 6.4 gm of methyl 2-[4-(4-chlorophenoxy-methyl)-phenoxy]-propionate in 30 ml of methanol. The mixture was thoroughly shaken, then an additional 20 ml of 1 N of sodium methylate solution were added, and the mixture was allowed to stand overnight. Thereafter, the reaction mixture was evaporated to about 10 ml in vacuo, the residue was taken up in water, and the aqueous solution was acidified with 2 N hydrochloric acid. The precipitate formed thereby was collected by suction filtration, yielding 4.8 gm (75% of theory) of the compound of the formula

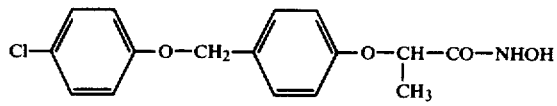

which had a melting point of 142° C.

EXAMPLE 46

Methyl ester of 2-[4-(4-Chlorophenoxy-methyl)-phenoxy]-propionic hydroxamic acid The hydroxamic acid obtained in Example 45 was reacted at room temperature with dimethyl sulfate in the presence of potassium hydroxide, and the reaction product was isolated and recrystallized from toluene, yielding 68% of theory of the methyl ester named in the heading, which had a melting point of 114°-115° C.

EXAMPLE 47

Ethyl 2-[4-(4-Chlorophenoxy-methyl)-phenoxy]-propionate (a) A solution of 23 gm (1 mol) of sodium in 400 ml of methanol was admixed at room temperature with 108 gm (1 mol) of 4-methyl-phenol. The mixed solution was boiled for two hours, and then the solvent was distilled off in a water aspirator vacuum. The residue was suspended in about 400 ml of toluene, the suspension was filtered, and the filtrate was evaporated in vacuo. The residue was dissolved in 800 ml of tetrahydrofuran, and the resulting solution was admixed over a period of 30 minutes with 181 gm (1 mol) of ethyl 2-bromo-propionate. The mixture was refluxed for 6 hours and then suction-filtered through diatomaceous earth at room temperature. The filtrate was washed with tetrahydrofuran, dried over sodium sulfate and evaporated in a water aspirator vacuum, leaving 248 gm of a light-brown oil which was distilled in a distillation column in an oil pump vacuum. 201.5 gm (96.7% of theory) of ethyl 2-(4-methyl-phenoxy)-propionate, m.p. 78°-82° C. at 0.11 mm Hg, were obtained.

(b) 20.8 gm (0.1 mol) of ethyl 2-(4-methyl-phenoxy)-propionate were dissolved in 60 ml of chloroform, the solution was heated to its boiling point, and then a solution of 6.8 ml (0.125 mol) of bromine in 20 ml of chloroform was added to the boiling solution over a period of 2 hours. During that time, the reaction time mixture was irradiated with a 200-watt light and vigorously stirred. The rate of addition of bromine was controlled in such a way that the reaction solution remained nearly colorless. The reaction solution was then boiled for another hour and was thereafter cooled to room temperature. The cool solution was now washed with ice water, then with a cold aqueous sodium bicarbonate solution and again with ice water, dried and evaporated, leaving 31.5 gm of a light-brown oil which was fractionated in a distillation column in an oil pump vacuum. 71% of theory of ethyl 2-(4-bromo-methyl-phenoxy)-propionate, b.p. 117°-124° C. at 0.14 mm Hg, were obtained.

(c) A solution of 2.3 gm (0.1 mol) of sodium in 100 ml of ethanol was admixed at room temperature with 12.8 gm (0.1 mol) of 4-chloro-phenol, and the resulting solution was heated to its boiling point for a short time and then allowed to cool to room temperature. A solution of 28.7 gm (0.1 mol) of ethyl 2-(4-bromomethyl-phenoxy)-propionate in 20 ml of ethanol was now added while thoroughly stirring, and the mixture was boiled for a few hours, then cooled to room temperature and suction-filtered through diatomaceous earth. The filtrate was evaporated, the viscous residue was suspended in 100 ml of isopropyl ether, the suspension was suction-filtered through diatomaceous earth, and the filtrate was evaporated. The oily residue was fractionally distilled in an oil pump vacuum, yielding 71% of theory of ethyl 2-[4-(4-chlorophenoxy-methyl)-phenoxy]-propionate, b.p. 185°–190° C. at 0.1 mm Hg.

The bromination in step (b) may also be carried out as follows:

17 gm (0.08 mol) of ethyl 2-(4-methyl-phenoxy)-propionate and 0.2 gm of 2,2'-azo-bis-(2-methyl-propionitrile) were dissolved in 100 ml of chloroform, and the solution was heated to its boiling point. One-half of a solution of 5.4 ml of bromine in 20 ml of chloroform was then added to the boiling solution over a period of 45 minutes. The reaction mixture was now cooled to about 40° C., an additional 0.2 gm of the catalyst was added, the mixture was again heated to its boiling point, and the other half of the chloroformic bromine solution was added. The mixture was kept boiling for two hours more and was then cooled to room temperature. The resulting reddish-brown solution was extracted three times with 100 ml each of a saturated aqueous sodium bicarbonate solution, the combined aqueous extracts were extracted twice with 50 ml each of methylene chloride, and the combined organic extracts were dried over sodium sulfate. The methylene chloride was now distilled off in a water aspirator vacuum, and the liquid evaporation residue was fractionally distilled in an oil pump vacuum, yielding 70% of theory of ethyl 2-(4-bromomethyl-phenoxy)-propionate, b.p. 128°–134° C. at 0.2 mm Hg.

EXAMPLE 48

2-[4-(4-Chlorophenoxy-methyl)-phenoxy]-propanol-(1)

2.0 gm of lithium aluminum hydride were admixed with 50 ml of absolute tetrahydrofuran, and a solution of 16.04 gm (50 millimols) of methyl 2-[4-(4-chlorophenoxymethyl)-phenoxy]-propionate in tetrahydrofuran was added dropwise to the mixture, while stirring. The resulting mixture was then refluxed for one hour, subsequently allowed to cool, and a misture of 20 ml of tetrahydrofuran and 20 ml of water was added dropwise. The slurry formed thereby was admixed with a sufficient amount of 2 N hydrochloric acid to dissolve the precipitated aluminum hydroxide, the solvent was distilled off in vacuo, and the residue was recrystallized from methanol/water, yielding 12.1 gm (83% of theory) of the compound of the formula

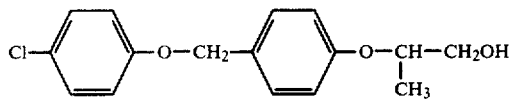

which had a melting point of 86° C.

EXAMPLE 49

2-[4-(2,4-Dichlorophenoxy-methyl)-phenoxy]-propanol-(1)

23 gm of sodium were dissolved in 100 ml of absolute ethanol, 26.9 gm of 4-(2,4-dichlorophenoxy-methyl)-phenol were added to the solution, 9.45 gm of 2-chloropropanol were added dropwise thereto, and the resulting mixture was boiled for 12 hours. Thereafter, the reaction solution was evaporated, the residue was taken up in water, and the aqueous solution was extracted with ether. The ethereal extract was washed with water, dried over sodium sulfate and evaporated, yielding 70% of theory of 2-[4-(2,4-dichlorophenoxy-methyl)-phenoxy]-propanol-(1), m.p. 34°–35° C.

As indicated above, we have discovered that the compounds embraced by formula I have very effective herbicidal properties. Particularly preferred are those compounds of the formula I wherein $R_1$ is chlorine or fluorine; $R_2$ is hydrogen or chlorine; and $R_3$ is —$CH_2OH$, —$COOR_6$ or —$COOCat$; where $R_6$ is hydrogen, alkyl of 1 to 6 carbon atoms, lower alkoxy-lower alkyl, lower alkenyl or lower alkynyl; and Cat is an alkali metal cation (for example, $Na^+$ or $K^+$), one equivalent of an alkaline earth metal cation or an ammonium cation, such as that which is derived from ammonia or from ammonium bases which are mono- or poly-substituted with methyl, ethyl, propyl, isopropyl or hydroxyethyl radicals.

Whenever we use the term "lower" in connection with hydrocarbon radicals, we intend to designate those with up to 4 carbon atoms. Particularly preferred are alkyl, alkoxy or alkylthio of 1 to 3 carbon atoms, especially 1 to 2 carbon atoms, alkyl and propargyl. Examples of unsubstituted and substituted alkyl radicals are methyl, ethyl, propyl, isopropyl, n-butyl, isobutyl, tert.butyl, methoxyethyl, ethoxyethyl, n-butoxyethyl and methoxy-ethoxy-ethyl.

The compounds of the formula I have a marked selective herbicidal effect, especially against weeds, such as meadow foxtail, wild oats, raygrass and wild millet. Selectivity is so pronounced that, even when higher quantities are used, dicotyledon food plants are only slightly affected. Even in some fields of monocotyledon food plants, such as corn, rice, barley or oats, weeds can be combatted with the active substances according to the present invention.

The compounds are suitable for application by the pre-germination method, as well as the post-germination method, the quantity used being 0.1 to 3 kg, preferably 0.3 to 1.5 kg/ha.

For herbicidal purposes, the compounds of the formula I are processed in known manner into customary formulations with conventional auxiliary and/or carrier substances, for example, into concentrates such as emulsion concentrates or wettable powders, where the active ingredient content is between about 10 and 95% by weight, or into dusting powders emulsions, granulates or solutions which are applied directly and contain between about 0.01 and 20% by weight of the active ingredient.

The concentrates are diluted with water to the desired concentration for application, generally about 0.01 to 3% by weight.

The following examples illustrate herbicidal compositions containing a compound of the formula I as an active ingredient.

EXAMPLE 50

Wettable powder

25% by weight 2-[4-(4-chlorophenoxymethyl)-phenoxy]-propionic acid,
55% by weight kaolin,
10% by weight colloidal silicic acid,
9% by weight calcium lignin sulfonate (dispersing agent),
1% by weight sodium tetrapropylenebenzene sulfonate (wetting agent).

The constituents are admixed and ground, and the powder is suspended in water for application in such a way that a concentration of active substance of 0.01 to 3% is obtained.

EXAMPLE 51

Dusting powder

1% by weight sodium 2-[4-chlorophenoxymethyl)-phenoxy]-propionate,
98% by weight talcum,
1% by weight methyl cellulose.

The constituents are admixed and ground homogeneously to make the dusting powder.

EXAMPLE 52

Emulsion concentrate

20% by weight ethyl 2-[4-(4-chlorophenoxymethyl)-phenoxy]-propionate, (or the corresponding methoxyethyl ester or methyl ester)
70% by weight liquid solvent mixture of high-boiling point aromatic hydrocarbons (Shellsol A),
6.5% by weight Tensiofix AS (emulsifier)
3.5% by weight Tensiofix DS (emulsifier).
emulsion concentrate is prepared from the constituents in the conventional way.

For some purposes of application, it may be appropriate to add other herbicides to the compounds according to the invention. Examples of such herbicides which can be added to achieve further advantages and effects are the following:

2,3,6-trichlorobenzoic acid and its salts,
2,3,5,6-tetrachlorobenzoic acid and its salts,
2-methoxy-3,5,6-trichlorobenzoic acid and its salts,
2-methoxy-3,6-dichlorobenzoic acid and its salts,
2-methyl-3,6-dichlorobenzoic acid and its salts,
2,3-dichloro-6-methylbenzoic acid and its salts,
2,4-dichlorophenoxyacetic acid and its salts and esters,
2,4,5-trichlorophenoxyacetic acid and its salts and esters,
2-methyl-4-chlorophenoxyacetic acid and its salts and esters,
2-(2,4,5-trichlorophenoxy)-propionic acid and its salts and esters,
2-(2,4-dichlorophenoxy)-butyric acid and its salts and esters,
4-(2-methyl-4-chlorophenoxy)-butyric acid and its salts and esters,
2,3,6-trichlorophenylacetic acid and its salts,
3,6-endoxohexanehydrophthalic acid, dimethyl-2,3,5,6-tetrachloroterephthalate, trichloroacetic acid and its salts,
2,2-dichloropropionic acid and its salts,
2,3-dichloropropionic acid and its salts, ethyl-N,N-di-(n-propyl)-thiolcarbamate, propyl-N,N-di-(n-propyl)-thiolcarbamate, ethyl-N-ethyl-N-(n-butyl)-thiolcarbamate, propyl-N-ethyl-N-(n-butyl)-thiolcarbamate,
2-chloroallyl-N,N-diethyldithiocarbamate,
N-methyldithiocarbamic acid salts,
S-ethylhexahydro-1H-azepine-1-carbothioate,
S-4-chlorobenzyl-N,N-diethylthiocarbamate, isopropyl-N-phenylcarbamate, isopropyl-N-(m-chlorophenyl)-carbamate,
4-chloro-2-butyl-N-(m-chlorophenyl)-carbamate, methyl-N-(3,4-dichlorophenyl)-carbamate, methylsulfanilyl carbamate, dinitro-o-(sec.-butyl)-phenol and its salts, pentachlorophenol and its salts,
3-(4-isopropylphenyl)-1,1-dimethyl-urea,
3-(3,4-dichlorophenyl)-1,1-dimethyl-urea,
3-phenyl-1,1-dimethyl-urea,
3-(3,4-dichlorophenyl)-3-methoxy-1,1-dimethyl-urea,
3-(4-chlorophenyl)-3-methoxy-1,1-dimethyl-urea,
3-(3,4-dichlorophenyl)-1-n-butyl-1-methyl-urea,
3-(3,4-dichlorophenyl)-1-methoxy-1-methyl-urea,
3-(4-chlorophenyl)-1-methoxy-1-methyl-urea,
3-(3,4-dichlorophenyl)-1,1,3-trimethyl-urea,
3-(3,4-dichlorophenyl)-1,1-diethyl-urea,
1-(2-methylcyclohexyl)-3-phenyl-urea,
1-(5-tert.-butyl-1,3,4-thiodiazol-2-yl)-1,3-dimethyl-urea,
3-(3-chloro-4-methylphenyl)-1,1-dimethyl-urea,
3-(3-chloro-4-methoxyphenyl)-1,1-dimethyl-urea, dichloro-urea,
2-chloro-4,6-bis-(ethylamino)-S-triazine,
2-chloro-4-ethylamino-6-isopropylamino-S-triazine,
2-methoxy-4,6-bis-(isopropylamino)-S-triazine,
2-methylmercapto-4,6-bis-(isopropylamino)-S-triazine,
2-methylmercapto-4,6-bis-(ethylamino)-S-triazine,
2-methylmercapto-4-ethylamino-6-isopropylamino-S-triazine,
2-chloro-4,6-bis-(isopropylamino)-S-triazine,
2-methoxy-4,6-bis-(ethylamino)-S-triazine,
2-methoxy-4-ethylamino-6-isopropylamino-S-triazine,
2-methylmercapto-4-(2-methoxyethylamino)-6-isopropylamino-S-triazine,
2-(4-chloro-6-ethylamino-5-triazin-2-yl)-amino-2-methylpropionitrile,
4-amino-6-tert.-butyl-3-methylthio-1,2,4-triazine-5(4H)-one,
3-cyclohexyl-6-dimethylamino-1-methyl-5-triazine-2,4-(1H,3H)-dione,
3-methyl-4-amino-6-phenyl-1,2,4-triazine-5-(4H)-one,
2,4-dichloro-4'-nitrodiphenyl ether,
2,4,6-trichloro-4'-nitrodiphenyl ether,
2,4-dichloro-6-fluoro-4'-nitrodiphenyl ether,
3-methyl-4'-nitrodiphenyl ether,
3,5-dimethyl-4'-nitrodiphenyl ether,
2,4'-dinitro-4-trifluoromethyldiphenyl ether,
2,4-dichloro-3'-methoxy-4'-nitrodiphenyl ether,
2-chloro-4-trifluoromethyl-4'-nitrodiphenyl ether,
2-chloro-4-trifluoromethyl-3'-ethoxy-4'-nitrodiphenyl ether,
2-chloro-4-trifluoromethyl-3'-carbethoxy-4'-nitrodiphenyl ether,
2-chloro-4-trifluoromethyl-3'-(1-carbethoxy)-ethoxy-4'-nitrodiphenyl ether,
N-(3,4-dichlorophenyl)-propionamide,
N-(3,4-dichlorophenyl)-methacrylamide,
N-(3-chloro-4-methylphenyl)-2-methylpentanamide,
N-(3,4-dichlorophenyl)-trimethylacetamide,
N-(3,4-dichlorophenyl)-α-α-dimethylvaleramide,
N-isopropyl-N-phenylchloroacetamide,
N-n-butoxymethyl-N-(2,6-diethylphenyl)-chloroacetamide,
N-n-methoxymethyl-N-(2,6-diethylphenyl)-chloroacetamide,
5-bromo-3-S-butyl-6-methyluracil,
5-bromo-3-cyclohexyl-1,6-dimethyluracil,
3-cyclohexyl-5,6-trimethylene uracil,
5-bromo-3-isopropyl-6-methyluracil,
3-tert.-butyl-5-chloro-6-methyluracil,
2,6-dichlorobenzonitrile,
diphenylacetonitrile,
3,5-dibromo-4-hydroxybenzonitrile,
3,5-diiodo-4-hydroxybenzonitrile,
2-chloro-N,N-diallylacetamide, N-(1,1-dimethyl-2-propionyl)-3,5-dichlorobenzamide
maleic acid hydrazide,
3-amino-1,2,4-triazole,
monosodium methane arsonate,
disodium ethane arsonate,
N,N-dimethyl-α-α-diphenylacetamide,
N,N-di-(n-propyl)-2,6-dinitro-4-trifluoromethyl)-aniline,
N,N-di-(n-propyl)-2,6-dinitro-4-methyl-aniline,
N,N-di-(n-propyl)-2,6-dinitro-4-methylsulfonyl-aniline,
O-(2,4-dichlorophenyl)-O-methylisopropylphosphoramidothioate,
4-amino-3,5,6-trichloropicolinic acid,
2,3-dichloro-1,4-naphthoquinone,
Di-(methoxythiocarbonyl)-disulfide,
3-isopropyl-1H-2,1,3-benzothiadiazin-(4)3H-on-2,3-dioxide,
6,7-dihydrodipyridol[1,2-a:2';1'-c]-pyrazidinium salts,
1,1'-dimethyl-4,4'-bipyridinium salts,
3,4,5,6-tetrahydro-3,5-dimethyl-2-thio-2H-1,3,5-thiadiazine,
1,2-dimethyl-3,5-diphenylpyrazoliummethyl sulfate,
N-sec.-butyl-2,6-dinitro-3,4-xylidine,
N-sec.-butyl-4-tert.-butyl-2,6-dinitroaniline,
$N^3,N^3$-diethyl-2,4-dinitro-6-trifluoromethyl-1,3-phenylene diamine,
1,1,1-trifluoro-(4'-phenylsulfonyl)-methanesulfono-o-toluidine,
2-(1-naphthoxy)-N,N-diethylpropionamide,
2-tert.-butyl-4-(2,4-dichloro-5-isopropoxyphenyl)-1,3,4-oxadiazolin-5-one,
4-chloro-5-methylamino-2-(α,α,α-trifluoro-m-tolyl)-3(2H)pyridazinone,
N-cyclopropylmethyl-α,α,α-trifluoro-2,6-dinitro-N-propyl-p-toluidine, and
N-phosphonomethyl-glycine.

Growth regulators, also, can be combined with the herbicides according to the invention, for example:
Maleic acid hydrazide and its salts,
9-hydroxyfluorenic-9-carboxylic acid, its salts and esters,
2-chloro-9-hydroxyfluorenic-9-carboxylic acid, its salts and esters,
1-(4-chlorophenyl)-1,2-dihydro-4,6-dimethyl-2-oxonicotinic acid and its salts,
4-methyl-3-(trifluoromethylsulfonyl)-amido-acetanilide, and
2,4-dimethyl-5-(trifluoromethylsulfonyl)-amido-acetanilide.

If mixtures of herbicides are used, the relative quantities in which they are employed are governed by the food plant cultures to be treated and the type of weeds to be combatted.

An extension of the possible uses of the herbicides and herbicidal combinations according to the invention can be achieved by the addition of such substances as do not substantially prejudice the desired effect, yet increase compatibility for the food plants ("synergists").

Admixture with certain carboxylic acid amides as synergists is proposed, to improve selectivity, for herbicides which are especially intended for combatting broadleafed weeds. Thus, in German Offenlegungsschrift 2,218,097 carboxylic acid amides have been described as synergists for a series of herbicidal thiocarbamates, acetanilides, triazines and 2,4-dichlorophenoxy acetic acid. According to German Offenlegungsschrift 2,402,983, synergists of the same type are suitable for improving the selectivity of herbicidal chloroacetanilides. A further group of synergists based on alkane sulfonates has been described in German Offenlegungsschrift 2,141,586 for protecting grains in the application of herbicidal thiolcarbamates and triazines. Another group of synergists which can be used in conjunction with thiocarbamate herbicides is derived from 2,3-dibromopropionamide.

We have discovered that the known synergists are also suitable for improving the selectivity of the herbicidal agents of the formula I.

A further object of the invention is, therefore, a method of selectively combatting weeds, especially in corn, rice, wheat and other cereal grains, which is characterized in that a herbicide of formula I is applied, optionally in admixture with known herbicides, in conjunction with a synergist
(a) of the formula

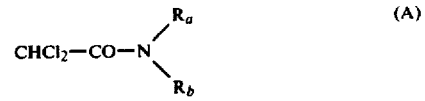

in which
R_a is hydrogen, a straight-chain or branched alkyl group with 1 to 5 carbon atoms, optionally substituted by halogen and/or by a cyano or a cycloalkyl group with 3 to 6 carbon atoms, an alkenyl or alkynyl group with 3 to 5 carbon atoms, or an optionally halogenated alkoxyalkyl, dialkoxyalkyl or alkenloxyalkyl group with up to 6 carbon atoms,
R_b is a straight-chain or branched alkyl group with 1 to 5 carbon atoms, optionally substituted by halogen and/or substituted by a cyano or a cycloalkyl group with 3 to 6 carbon atoms, an alkenyl or alkynyl group with 3 to 5 carbon atoms, an optionally halogenated alkoxyalkyl, dialkoxyalkyl or alkenyloxyalkyl group with up to 6 carbon atoms or a cycloalkyl group with 3 to 6 carbon atoms optionally substituted by an ethenyl or ethynyl group; and
R_a and R_b, together with each other and the nitrogen atom, represent a 5 to 7-membered heterocycle which may contain an oxygen, nitrogen or sulfur atom and may be substituted once or several times by lower alkyl; or
(b) of the formula

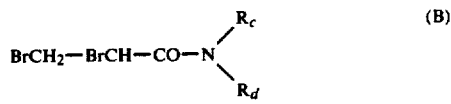

in which
R_c is hydrogen, an alkenyl or alkyl group with up to 5 carbon atoms,
R_d is an alkyl, alkenyl or alkynyl group with up to 6 carbon atoms, a dialkoxyalkyl group with up to 6 carbon atoms or cycloalkyl group with 3 to 6 carbon atoms optionally substituted by an ethenyl or ethynyl group; and
R_c and R_d, together with each other and the nitrogen atom, and optionally with a further nitrogen atom, an oxygen atom or a sulfur atom, represent a heterocycle optionally substituted, once or several times, by lower alkyl; or (c) of the formula $$Y—(CH_2)_m—O—SO_2Q \qquad (C)$$

in which m is an integer from 1 to 6,
  Q is an optionally halo-substituted alkyl group with up to 6 carbon atoms, an acetoxy-lower alkyl, an acetoxy-halo-lower alkyl or aryl group, and
  Y is chlorine or bromine.

Application is carried out in the manner conventional for synergists, i.e. it can take place simultaneously with the herbicide, in which case herbicide and synergist are produced in the form of common formulations or sprays made from them. Active substance and synergist can, however, also be applied in the form of a tank mixture. Separate application also is possible, especially for treatment of the cultivated area before sowing or after sowing, with the synergist and then with the herbicide. Application can also take place by first applying the herbicide and shortly afterwards the synergist.

Those compounds of the formula A have preference in which $R_a$ is an unsaturated group, primarily the allyl group, and $R_b$ stands for allyl, ethyl or propyl. Insofar as $R_a$ and $R_b$, together with the nitrogen atom, represent a heterocycle, this is preferably a 2,2-dimethyl-1,3-oxyzolidinyl, pyrrolidinyl, piperidinyl or morpholinyl group.

Those compounds of the formula B have preference in which $R_c$ is hydrogen, ethyl or allyl, and $R_d$ stands for a branched alkyl group, especially tert.-butyl, isopropyl, 3-methyl-3-butinyl,4-methyl-2-pentyl or for allyl, 2,2-dimethoxy-ethyl, 2-ethyl butyl or 1-ethynylcyclohexyl.

Those synergists of the formula C have preference in which X is bromine, m is 2 or 3, and Q is methyl or ethyl.

The herbicides are applied in the same quantity as is proposed for application without synergist.

The compatibility improved by the addition of synergists enables even higher quantities than conventional to be used, however. This can be advantageous when with the higher quantity even those undesirable plants can be attacked which otherwise could not be combatted sufficiently; or when a more complete or more certain effect is to be achieved under conditions which are very unfavorable for the application of herbicides.

The weight ratio of synergist to herbicidally active substance is between 1:10 and 10:1, preferably 1:6 to 2:1, especially 1:4 to 1:1.

The formulation of active substance and synergist takes place in the manner conventional for herbicides with customary auxiliary and carrier substances, for example, in the form of wettable powders, emulsifiable concentrates, granulates and dusting powders.

TEST DESCRIPTION:

Method: Corn of the "Harrach" variety is sown in plastic cups of 12 cm diameter in cultivated gardener's earth and receives a covering layer of clean sand. Immediately after sowing, the test preparations or tank mixtures of herbicides with synergist are applied in a series of doses and in mixtures in varying conditions with a laboratory spraying unit in 1200 liters/ha water. Set-up in the greenhouse at 23° C. by day and 18° C.±2° C. by night.

After the corn has reached a height of 15 cm in the untreated control, the plants are cut off and weighed. The fresh weight is the criterion of the herbicidal effect and is expressed in % of the control. Dose-effect curves enable the effective dose to be made up (ED 10-50).

See table for result: limiting dosage for compatibility of test preparations and combinations on corn in kg/ha active substance. Result from 2 tests.

| Herbicide | Synergist | Ratio | Test 1 Limiting ED 30 | Test 2 dosage ED 50 |
|---|---|---|---|---|
| I | | | 0.2 | 0.4 |
| I + | A | 1:1 | 0.9 | — |
| I + | A | 1:0.25 | 0.9 | 2.0 |
| II | | | 0.3 | 0.3 |
| II + | A | 1:1 | — | 3.0 |
| II + | A | 1:0.5 | 1.2 | 3.0 |

I: 2-[4-(4-chlorophenoxymethyl)-phenoxy]-propionic acid
II: methyl 2-[4-(4-chlorophenoxymethyl)-phenoxy]-propionate
A: N,N-diallyldichloroacetamide.

By mixing the synergist A, the compatible limiting dosage of the herbicides is increased by 3-10 times.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A method of killing weeds which comprises contacting said weeds with an effective amount of a selective herbicidal composition consisting essentially of a liquid or solid inert carrier and an herbicidally effective amount of a compound of the formula

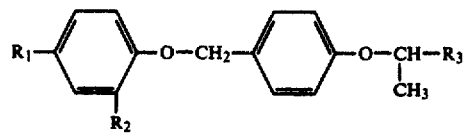

wherein $R_1$ and $R_2$ are each hydrogen, chlorine or fluorine; and
  $R_3$ is —COOH, —COOCat or —COOR$_6$; where Cat is one equivalent of an inorganic or organic cation; and
  $R_6$ is alkyl of 1 to 10 carbon atoms which may optionally have a chloro, hydroxyl, lower alkoxy, lower alkoxy-lower alkoxy, lower alkylthio, amino, mono-lower alkyl-amino, di-lower alkyl-amino, allyloxy- or phenoxy-substituent attached thereto; phenyl; benzyl; monochlorobenzyl; di-chloro-benzyl; cyclohexyl; 1-ethynylcyclohexyl; lower alkenyl; lower alkynyl; 2-(2',4',5'-trichlorophenoxy)-ethyl; 2-(2',5'-dichloro-4'-bromo-phenoxy)-ethyl; or

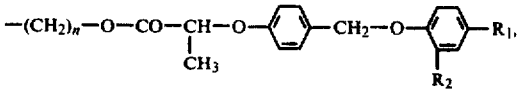

where $R_1$ and $R_2$ have the meanings defined above, and n is an integer from 2 to 6, inclusive.

2. The method according to claim 1 where said compound is 2-[4-(4-chlorophenoxymethyl)-phenoxy]-propionic acid, a salt thereof or a lower alkyl ester thereof.

* * * * *